United States Patent
Sato et al.

(10) Patent No.: US 7,537,684 B2
(45) Date of Patent: May 26, 2009

(54) SAMPLE ANALYZING METHOD AND SAMPLE ANALYZING DEVICE

(75) Inventors: Yoshiharu Sato, Kyoto (JP); Koji Katsuki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 430 days.

(21) Appl. No.: 10/522,394

(22) PCT Filed: Jul. 23, 2003

(86) PCT No.: PCT/JP03/09357

§ 371 (c)(1),
(2), (4) Date: Jan. 25, 2005

(87) PCT Pub. No.: WO2004/011921

PCT Pub. Date: Feb. 5, 2004

(65) Prior Publication Data

US 2006/0224658 A1    Oct. 5, 2006

(30) Foreign Application Priority Data

Jul. 25, 2002 (JP) .............................. 2002-216314

(51) Int. Cl.
*G01N 27/327* (2006.01)

(52) U.S. Cl. .................. 205/777.5; 204/403.02; 204/406

(58) Field of Classification Search ............ 204/403.01, 204/403.02, 406; 205/777.5, 778, 792
See application file for complete search history.

(56) References Cited

U.S. PATENT DOCUMENTS

| | | | |
|---|---|---|---|
| 5,352,351 A | | 10/1994 | White et al. |
| 5,620,579 A | * | 4/1997 | Genshaw et al. ............ 204/402 |
| 7,232,510 B2 | * | 6/2007 | Miyazaki et al. ....... 204/403.01 |

2005/0258034 A1 * 11/2005 Iketaki et al. .......... 204/403.01

FOREIGN PATENT DOCUMENTS

| | | |
|---|---|---|
| EP | 1074832 | 4/1993 |
| EP | 0 732 406 A1 | 9/1996 |
| JP | 5-196596 | 8/1993 |
| JP | 06-109688 | 4/1994 |
| JP | 8-502589 | 3/1996 |
| JP | 8-320304 | 12/1996 |

(Continued)

*Primary Examiner*—Kaj K Olsen
(74) *Attorney, Agent, or Firm*—Hamre, Schumann, Mueller & Larson, P.C.

(57) ABSTRACT

This invention relates to a technique for analyzing a sample. A sample analyzer (1) provided by the invention includes: a voltage applier (12) for applying a voltage to a reaction field which includes a sample; a response measurer (13) for measurement of a response to the voltage applied to the reaction field; a selector (11) for selecting a first voltage application state for measurement of a first response for use in calculation necessary for analyzing the sample or a second voltage application state for measurement of a second response for use in determining whether or not the reaction field has been supplied with a target amount of the sample; an arithmetic operator (17) for calculation necessary for analyzing the sample based on the first response; a determiner (17) for determination, based on the second response, on whether or not the reaction field has been supplied with the target amount of sample; and a controller (15) which makes the selector select the second voltage application state after making the selector select the first voltage application state.

16 Claims, 5 Drawing Sheets

FOREIGN PATENT DOCUMENTS

| | | | | | |
|---|---|---|---|---|---|
| JP | 2000-162176 | 6/2000 | WO | WO 01/33216 | 5/2001 |
| JP | 2001-66279 | 3/2001 | WO | WO 01/75438 | 10/2001 |
| JP | 2001-330581 | 11/2001 | WO | WO 02/44705 | * 6/2002 |

* cited by examiner

SAMPLE ANALYZING METHOD AND SAMPLE ANALYZING DEVICE

The present application is a 35 USC 371 national stage entry of PCT/JP03/09357 filed on Jul. 23, 2003.

TECHNICAL FIELD

The present invention relates to a technique for analyzing samples.

BACKGROUND ART

As a common method for analyzing samples, an oxidation-reduction reaction is used. An example is a quantitative procedure disclosed in JP-A2001-330581, which makes use of a biosensor that provides a liquid reaction field.

As will be expected from FIG. 6 of the present application, the biosensor disclosed in the gazette makes use of a capillary which is formed by laminating a cover 92 onto a substrate 90 via a spacer 91, for measurement of blood sugar level. The substrate 90 has a surface formed with a working electrode W, a counter electrode C and a liquid junction sensing electrode S. Though not illustrated in the figure, a reagent region is provided so as to bridge at least an end of the working electrode W with an end of the counter electrode C. The reagent region includes an oxidation-reduction enzyme and an electron transfer material.

In this biosensor 9, when blood is introduced into the capillary, a liquid reaction field is formed which includes the oxidation-reduction enzyme, the electron transfer material and glucose, in the capillary. In the liquid reaction field, electron transfer takes place between glucose and the electron transfer material. The electron transfer material becomes a reductant (or an oxidant). Then, when a voltage is applied to the liquid reaction field via the working electrode W and the counter electrode C, electron transfer takes place between the working electrode W and the reductant (oxidant), which generates a response current necessary for analyzing the sample. On the other hand, by applying a voltage to the liquid reaction field via the liquid junction sensing electrode S and the working electrode W (or the counter electrode C), it is possible to obtain a response current necessary for detecting whether or not the capillary has been filled with the sample. The voltage application via the liquid junction sensing electrode S and the working electrode W (or the counter electrode C) ceases if the response current for detection exceeds a predetermined value. Specifically, if a liquid junction is detected between the liquid junction sensing electrode S and the working electrode W (or the counter electrode C), blood has already reached the liquid junction sensing electrode S. So, detection of a liquid junction justifies an assumption that the capillary has been filled with the sample.

However, according to the quantitative procedure described above, the response current for detection is obtained simultaneously with the obtainment of the response current for analysis. In other words, a voltage is applied to the liquid reaction field simultaneously, for a different purpose than obtaining a response current for analysis, using the liquid junction sensing electrode S. During this process, part of glucose which is supposed to be used for the measurement of response current for analysis is used for the detection of sample supply. Further, this causes non-uniformity in the concentration of glucose or reductant (oxidant) in the reaction field. As a result, the response current for analysis does not necessarily reflect the glucose concentration appropriately. Further, severity of non-uniformity is not always the same, which leads to a problem of decreased measuring accuracy.

DISCLOSURE OF THE INVENTION

An object of the present invention is to make possible to detect whether or not a target amount of sample has been supplied to the reaction field, without sacrificing accuracy of the analysis.

A first aspect of the present invention provides a sample analyzing method. In this method, an analysis of a sample is made based on a response obtained upon application of a voltage to a reaction field which contains the sample. The method includes a first step for measuring a first response for use in calculation necessary for analyzing the sample, and a second step performed later than the first step for measuring a second response necessary to determine whether a target amount of the sample has been supplied to the reaction field.

In the first and the second steps, the first and the second responses are measured as electric currents. The first and the second responses may of course be measured in the form of voltage, electric capacitance, quantity of light, and so on.

In the first and the second steps, the application of voltage to the reaction field is made by using two electrodes selected from three or more electrodes. In this case, a combination of two electrodes selected in the first step is different from a combination of two electrodes selected in the second step.

In the sample analyzing method according to the present invention, use is preferably made of an analyzing tool which includes a substrate provided with a capillary for moving the sample and the three or more electrodes, wherein each of the electrodes has a respective part lined up in the capillary in a direction of the sample movement. In this case, at least one of the two electrodes selected for measurement of the second response in the second step has its part disposed downstream of the sample flow from the two electrodes selected in the first step.

Preferably, the sample analyzing method according to the present invention further includes a third step of determining whether or not the sample has moved in the reaction field while carrying out the first step.

In the first step, the first response is measured at a plurality of measuring points at every predetermined time interval. With this, the determination in the third step on whether or not the sample has moved in the reaction field is made by checking a time course of the responses obtained from the measuring points to see whether or not a first peak which appears first is followed by a second peak.

If the first response is measured as a response current at each of the measuring points, the determination in e.g. the third step on whether or not the second peak has appeared is made as follows. Specifically, a response current measured at one of the measuring points is compared with a response current measured at another of the measuring points located right before that one measuring point in the time course, to see if the response current at that one measuring point exceeds the response current at that another measuring point by a predetermined or greater value.

Alternatively, in the third step, the determination on whether or not the sample has moved in the reaction field may be made by checking a time course of accumulated response values obtained from each measuring point to see whether or not there has appeared an inflexion point.

A second aspect of the present invention provides a sample analyzing method based on a response obtained upon application of a voltage to a reaction field containing the sample. The method includes a step of measuring a response at a plurality of measuring points at every specific time interval for use in calculation necessary for analyzing the sample, and an additional step of determining whether or not the sample has moved in the reaction field. The determination in the additional step on whether or not the sample has moved in the reaction field is made by checking a time course of the responses obtained from the measuring points to see whether or not a first peak which appears first is followed by a second peak.

The response is measured e.g. as a response current at each of the measuring points. In this case, the determination in the additional step on whether or not the second peak has appeared is made as follows. Specifically, a response current measured at one of the measuring points is compared with a response current measured at another of the measuring points located right before that one measuring point in the time course, to see if the response current at that one measuring point exceeds the response current at that another measuring point by a predetermined or greater value.

A third aspect of the present invention provides a sample analyzing method of analyzing a sample based on a response obtained upon application of a voltage to a reaction field containing the sample. The method includes a step of measuring a response at a plurality of measuring points at every specific time interval for use in calculation necessary for analyzing the sample, and an additional step of determining whether or not the sample has moved in the reaction field. The determination in the additional step on whether or not the sample has moved in the reaction field is made by checking a time course of accumulated response values obtained from each measuring point to see whether or not there has appeared an inflexion point.

A fourth aspect of the present invention provides a sample analyzer which includes: a voltage applier for application of a voltage to a reaction field including a sample; a response measurer for measurement of a response to the voltage applied to the reaction field; a selector for selecting a first voltage application state for measurement of a first response for use in calculation necessary for analyzing the sample, or a second voltage application state for measurement of a second response for use in determining whether or not the reaction field has been supplied with a target amount of the sample; an arithmetic operator for calculation necessary for analyzing the sample based on the first response; a determiner for determination based on the second response, on whether or not the reaction field has been supplied with the target amount of sample; and a controller for causing the selector to select the second voltage application state after causing the selector to select the first voltage application state.

The measurer measures e.g. the first and the second responses as electric currents in the first and the second steps.

The sample analyzer according to the present invention utilizes an analyzing tool which includes a substrate, a capillary for moving the sample and three or more electrodes formed in the substrate. Part of each electrode line up in the capillary in a direction of the sample movement. In this case, the voltage applier applies the voltage to the reaction field via two electrodes selected from the three or more electrodes. The controller controls the selector, when selecting the two electrodes for measurement of the second response, to include at least one electrode which has its part disposed downstream of the sample flow from the two electrodes selected for measurement of the first response.

The selector includes e.g. a switch for individual selection for the three or more electrodes, of a state in which the electrode is electrically connected with the voltage applier or a state in which it is not.

The sample analyzer according to the present invention further includes an additional determiner for determining whether or not the sample has moved in the reaction field while measuring the first response. In this case, it is preferable that the arithmetic operator recognizes an error if the determiner determines that there has not been a supply of a target amount of the sample, or if the additional determiner determines that there has been a movement of the sample, and yet, the arithmetic operator makes calculation necessary for analyzing the sample regardless of the error.

The sample analyzer according to the present invention may further include a display for displaying a result of calculation made by the arithmetic operator and an error message. In this case, preferably, the display displays a content of the error upon recognition of the error by the arithmetic operator.

It should be noted here that the "movement of the sample in the reaction field" includes a case where there has been an additional supply of the sample to the reaction field, and a case where the sample which has once moved and stopped moves again spontaneously or due to external force.

BEST MODE FOR CARRYING OUT THE INVENTION

Hereinafter, the best mode for embodying the present invention will be described specifically, with reference to the drawings.

Figure 1:
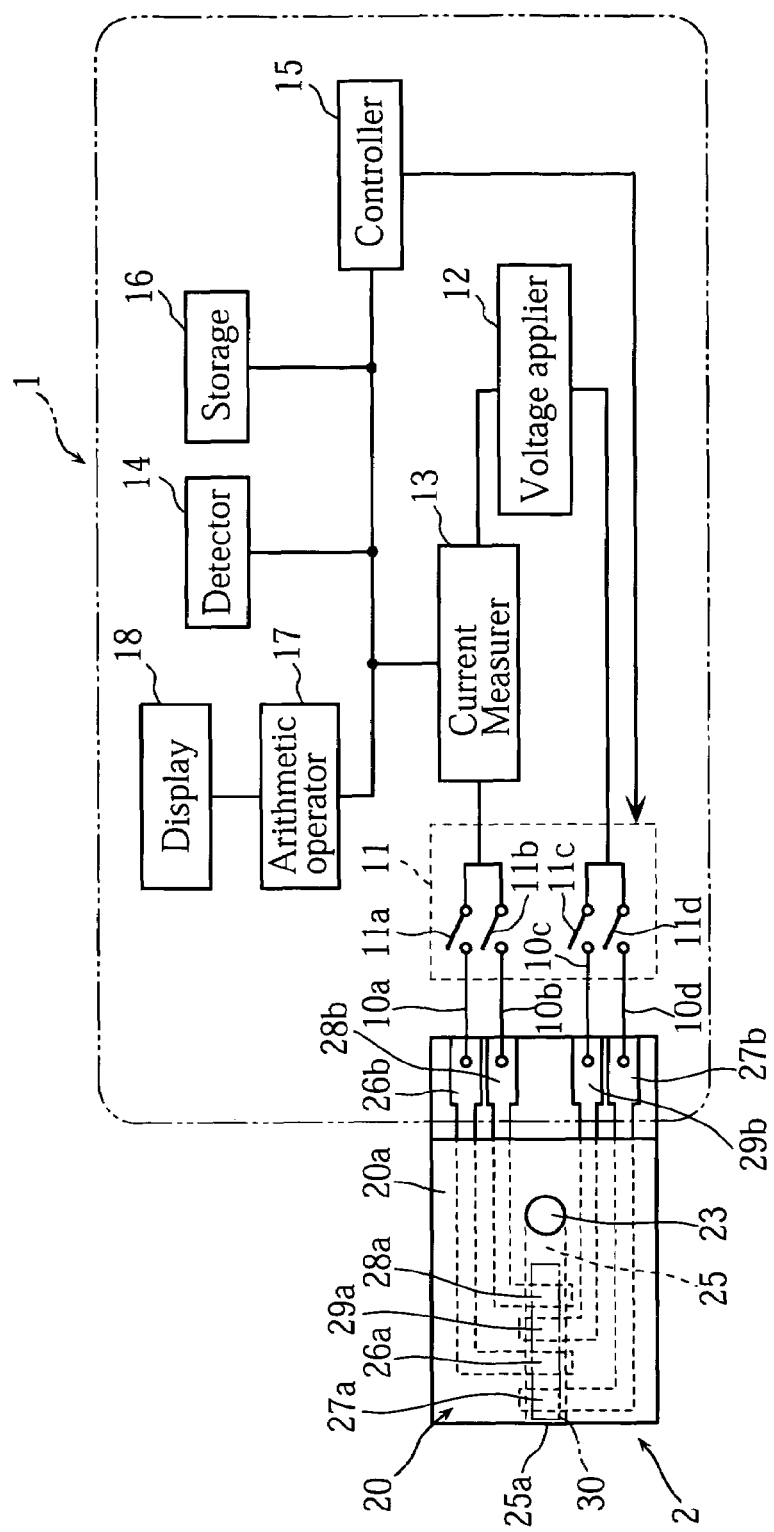
FIG. 1 shows a sample analyzer according to the present invention, mounted with a biosensor. The sample analyzer is shown in a block diagram whereas the biosensor is shown in a plan view.

FIG. 1 shows a sample analyzer 1 which measures a specific component in a sample, using a biosensor 2 attached thereto.

Figure 2:
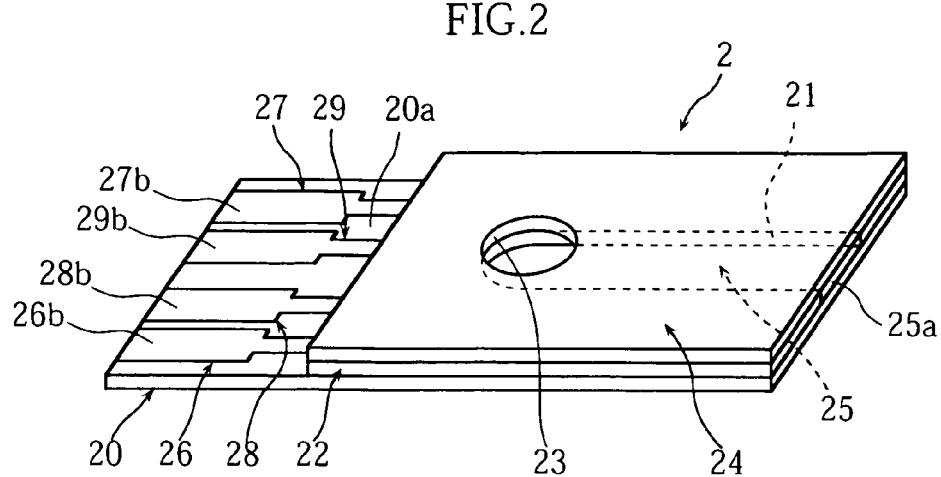
FIG. 2 is an overall perspective view of the biosensor in FIG. 1.
Figure 3:
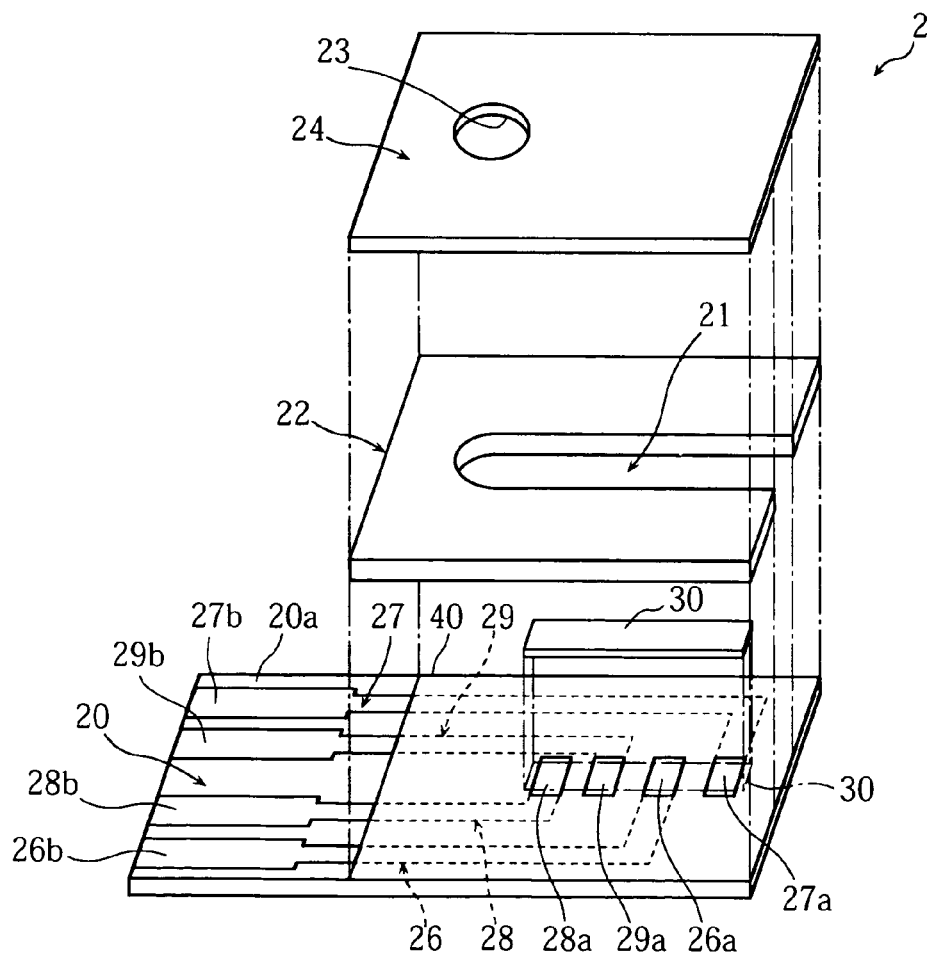
FIG. 3 is an exploded perspective view of the biosensor in FIG. 2.

As clearly shown in FIG. 2 and FIG. 3, the biosensor 2 includes a substrate 20 which has a first surface 20a laminated with a spacer 22 and a cover 24. The spacer 22 has a narrow slit 21. The cover 24 has a hole 23. With the spacer 22 and the cover 24 laminated on the first surface 20a of the substrate 20, the substrate 20, the spacer 22 and the cover 24 provide a capillary 25. The capillary 25 communicates with outside, via a sample inlet 25a and the hole 23. In other words, the biosensor 2 is able to supply a sample via the sample inlet 25a to the capillary 25, and the sample supplied from the sample inlet 25a is able to move by capillarity toward the hole 23 in the capillary 25.

The first surface 20a of the substrate 20 is provided with measuring electrodes 26, 27, detection electrodes 28, 29, and a reagent region 30. The reagent region 30 is a porous solid for example, easily soluble in water, and interconnects ends 26a, 27a, 28a, 29a of the electrodes 26-29. The reagent region 30 includes e.g. an oxidation-reduction enzyme and an electron transfer material in the form of oxide.

The reagent region 30 constructed as the above is dissolved by the sample as the sample is introduced from the sample inlet 25a and moves through the capillary 25. This establishes a liquid reaction field which makes contact with all of the electrodes 26-29, in the capillary 25. In this liquid reaction field, due to catalytic activity by the oxidation-reduction enzyme, a specific component in e.g. the sample is oxidized and the electron transfer material is reduced. When a voltage is applied to the liquid reaction field via the electrodes 26-29, the electron transfer material releases electrons, to become an oxide, and the amount of released electrons can be measured as a response current, by using the electrodes 26-29.

The sample analyzer 1 in FIG. 1 includes a terminal regions 10a-10d, a first through a fourth switches 11a-11d, a voltage applier 12, an electric current measurer 13, a detector 14, a controller 15, a storage 16, an arithmetic operator 17, and a display 18.

The terminal regions 10a-10d make contact with ends 26b-29b of the electrodes 26-29 when the biosensor 2 is attached to the sample analyzer 1.

The voltage applier 12, which applies a voltage to the liquid reaction field, is provided by a DC power source such as an ordinary dry battery or a rechargeable battery.

The electric current value measurer 13 measures a response current when the voltage is applied to the liquid reaction field.

The first through the fourth switches 11a-11d select the state of terminal regions 10a-10d, i.e. whether or not they are connected with the voltage applier 12 and the electric current measurer 13. Each of the switches 11a-11d is turned on and off individually by the controller 15. Therefore, by selecting the ON or OFF state for each of the switches 11a-11d, it is possible to select a combination of electrodes from the electrodes 26-29, for application of a voltage to the liquid reaction field.

The detector 14 detects whether or not it is possible to perform an analysis by using the biosensor 2. Specifically, the detector 14 detects whether or not the biosensor 2 has been attached to the sample analyzer 1, whether or not the sample has been introduced into the capillary 25, whether or not the capillary 25 has been filled with the sample, and whether or not the sample has been moved after the sample is introduced into the capillary 25. The controller 15 controls the switches 11a-11d as described above, as well as the detector 14, the arithmetic operator 17 and so on.

The storage 16 stores a variety of programs, calibration curve data and other data necessary for running the programs. The calibration curve data indicates a relationship between measured response current values (or voltage values obtained by converting the response current values, or accumulated quantity of electric charge obtained from the response current values) and the concentration of the specific component.

The arithmetic operator 17 calculates the concentration of the specific component in the sample, based on the response current measured by the electric current measurer 13.

The display 18 displays results of the calculation made by the arithmetic operator 17, error messages and so on. The display 18 is provided by a liquid crystal display device for example.

It should be noted here that each of the detector 14, the controller 15, the storage 16 and the arithmetic operator 17 can be provided by e.g. a CPU, a ROM, a RAM or combination thereof.

Figure 4:
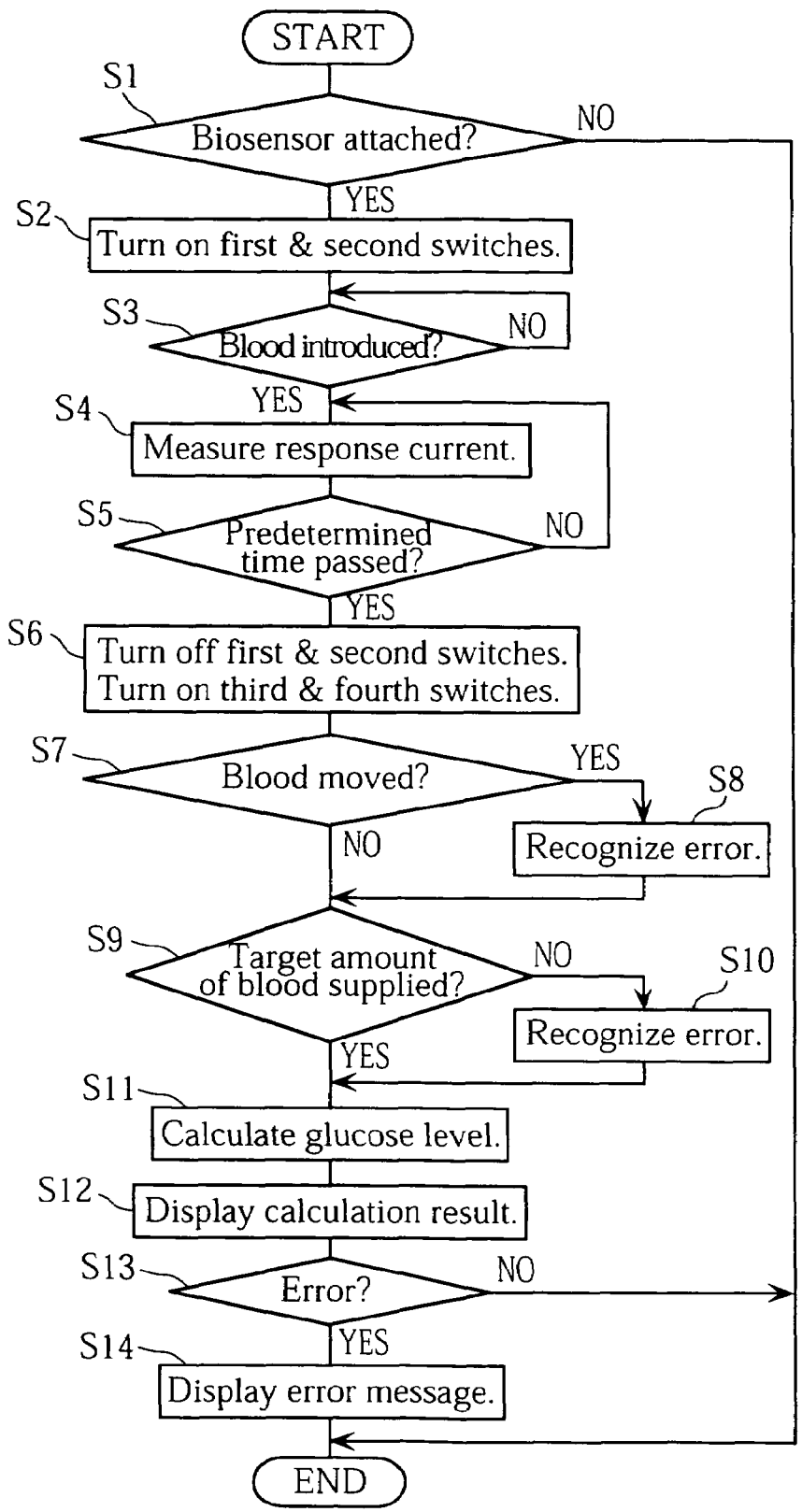
FIG. 4 is a flowchart for describing an operation in the sample analyzer.
Figure 5A:
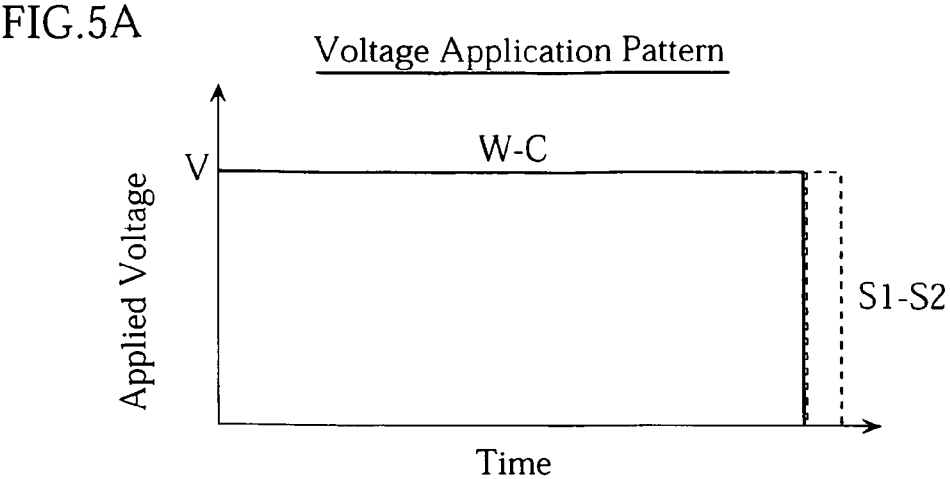
FIG. 5A is a graph showing a voltage application pattern in a sample analysis.

Hereinafter, description will cover how the biosensor 2 and the sample analyzer 1 may be used in an analyzing procedure. As an example, the description will take an amperometric method for a measurement of blood glucose level, with reference to FIG. 1, FIG. 4 and FIG. 5. Note that all of the first through the fourth switches 11a-11d are turned OFF before the analysis begins.

In the sample analyzer 1, first, a determination is made if the biosensor 2 is attached or not (S1). In the determination process, use is made of a sensor such as an optical sensor or a pressure sensor, and the detector 14 makes the determination based on an output from the sensor.

When the detector 14 determines that the biosensor 2 is attached to the sample analyzer 1 (S1: YES), the controller 15 turns on the first and the second switches 11a, 11d (S2). Under this state, a constant voltage V is applied between the measuring electrodes 26, 27 by the voltage applier 12 (See the solid line (W-C) in FIG. 5A).

Then, the detector 14 determines if the blood has been introduced into the capillary 25 (S3). The determination whether or not the blood has been introduced is made by checking whether or not a response current measured via the measuring electrodes 26, 27 has exceeded a predetermined threshold value $I_1$, (See FIG. 5B). In other words, the detection of the blood introduction into the capillary 25 is made by detecting electric conduction between the measuring electrodes 26, 27, i.e. by detecting whether or not the blood has reached a region where the electrodes 26, 27 are.

If the detector 14 determines that the blood has not been introduced into the capillary 25 (S3: NO), Step S3 is repeated until the introduction of blood has been detected. However, if Step S3 has been repeated for a predetermined number of times, or if the blood introduction is not detected within a predetermined duration of time, then the determination at Step S3 may be stopped and the program may go to an error processing routine.

On the contrary, if the detector 14 determines that the blood has been introduced into the capillary 25 (S3: YES), the electric current measurer 13 measures a response current at a predetermined time interval (S4).

In the capillary 25, the blood which is introduced dissolves the reagent region 30, and a liquid reaction field is formed in the capillary 25 which includes the oxidation reduction enzyme, the electron transfer material and glucose. In this liquid reaction field, electrons are taken out of the glucose for example, and these electrons are supplied to the electron transfer material, causing the electron transfer material to become a reductant. On the other hand, the liquid reaction field is applied with a voltage which results from an electric potential difference between the measuring electrodes 26, 27. Thus, the reductant releases electrons to the measuring electrode 26, and becomes an oxidant again. In such an electron transfer, a response current measured at the electric current measurer 13 is correlated with the amount of electrons released by the reductant, i.e. the amount of electrons taken out of the glucose, and thus the electric current reflects the glucose concentration.

If a response current has been measured (S4), the arithmetic operator 17 checks (S5) if a predetermined amount of time has been lapsed since the detection of the blood introduction (S3: YES). If Step S5 determines that the predetermined amount of time has not been passed (S5: NO), the electric current measurer 13 repeats the measurement of a response current (S4) until the arithmetic operator 17 determines that the predetermined amount of time has passed (S5: YES).

The time interval for the response current measurement is 0.02-0.2 sec. for example, and the measured response current values are stored in the storage 16, together with e.g. the time of measurement.

When the arithmetic operator 17 determines that the predetermined amount of time has passed (S5: YES), the first and the second switches 11a, 11d are turned off whereas the third and the fourth switches 11b, 11c are turned on (S6). Under this state, a constant voltage V is applied between the detection electrodes 28, 29 by the voltage applier 12 (See the broken line (S1-S2) in FIG. 5A).

Figure 5B:
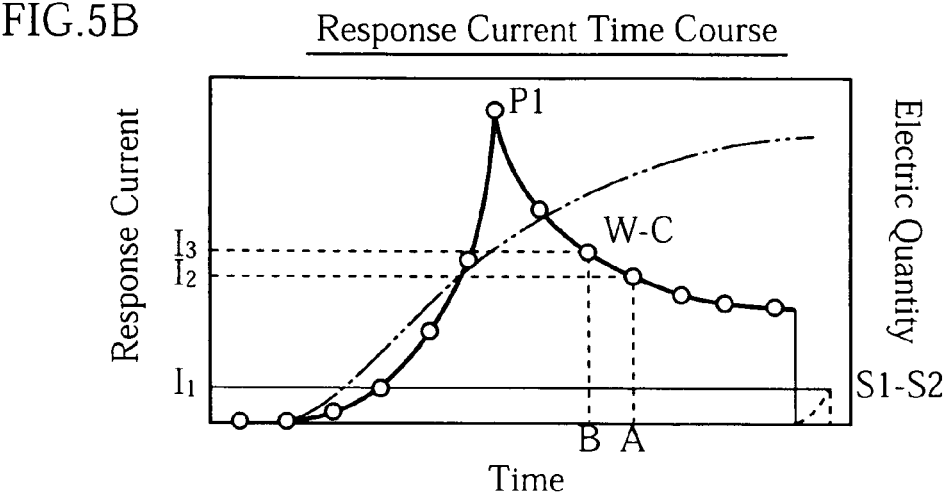
FIG. 5B is a graph showing time courses of a response current and an accumulated quantity of electric charge with respect to the voltage application pattern in FIG. 5A.
Figure 5C:
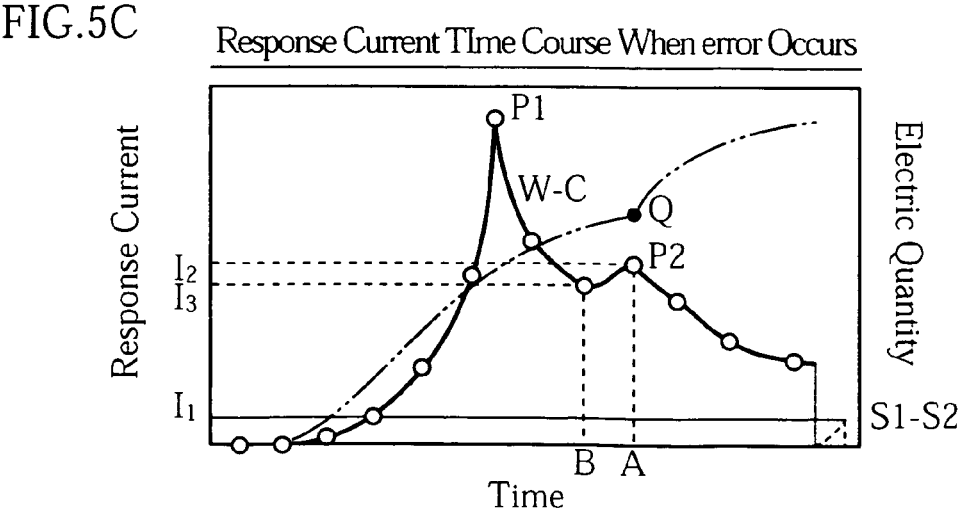
FIG. 5C is a graph showing time courses of a response current and an accumulated quantity of electric charge when there was an additional supply of sample.
Figure 6:
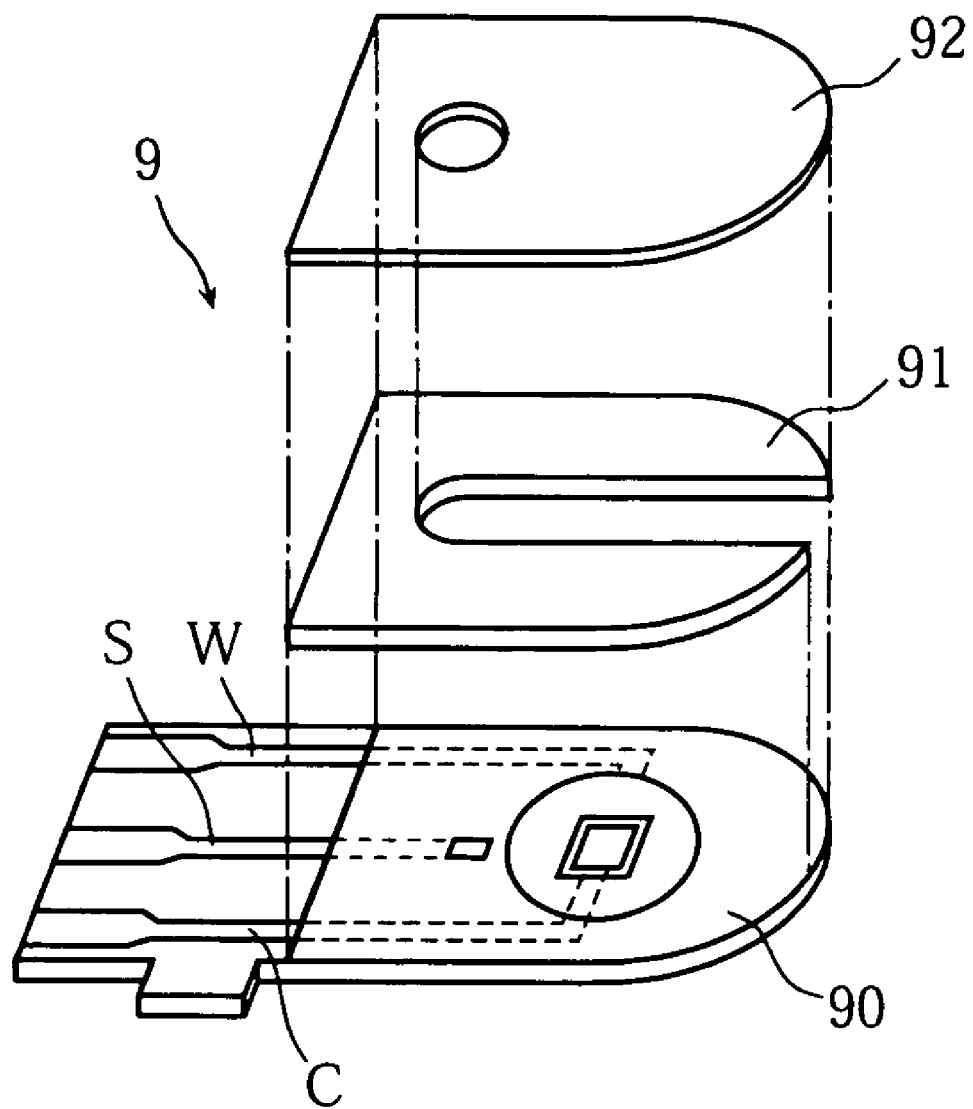
FIG. 6 is an exploded perspective view of a conventional biosensor.

On the other hand, the detector 14 determines if there has been a movement of blood in the capillary 25 (S7). The determination whether or not the blood has moved is made, for example, by checking a response current time course shown in FIG. 5B and FIG. 5C to see if the first peak P1 is followed by the second peak P2. If there is no blood movement, the response current decreases straightly with time, after reaching the first peak P1 as shown in FIG. 5B. On the contrary, if there is a blood movement, glucose concentration distribution changes in the capillary 25, and the glucose concentration increases around the end 26a of the measuring electrode 26. For this reason, if there is a blood movement, the response current increases upon the blood movement, resulting in the second peak P2 as shown in FIG. 5C. Therefore, by checking whether or not the second peak P2 appears, it is possible to determine if the blood has moved or not.

The blood movement phenomenon appears when, e.g. there has been an additional supply of blood to the capillary 25 after a blood introduction is detected in Step S3 (S3: YES), or when blood which has once stopped in movement resumes its movement spontaneously or due to application of external force such as vibration.

Detection of the second peak P2 is made by e.g. comparing a response current $I_2$ at each point of measurement A with a response current $I_3$ at a comparative point of measurement B which is a point right before the given point of measurement A. More specifically, if a response current $I_2$ at a point of measurement A is greater than a response current $I_3$ by a predetermined value, it is determined that the second peak P2 has appeared. With this arrangement, the detector 14 determines that there has been a blood movement in the capillary 25 if the second peak P2 has appeared (See FIG. 5C), while determining that there has not been a blood movement if the second peak has not appeared (See FIG. 5B).

It should be noted here that a response current at a point of measurement A can be greater than a response current at the comparative measuring point B due to noise or measurement errors, even if there has not been a blood movement. Such a phenomenon appears more significantly when measurements are made in a small time interval. If this poses a problem, the above-described predetermined value is set to include the influence by noise and measurement errors.

If the detector 14 determines that there has been a blood movement (S7: YES), the detector 14 recognizes that there has been an error in measurement due to the blood movement (S8). If the detector 14 determines that there has been no blood movement (S7: NO), or recognizes in Step S8 that there has been an error, the detector 14 checks if the capillary 25 has been supplied with a target amount of the blood (S9).

Whether or not the target amount of blood has been supplied is determined by checking if the capillary 25 is filled with the sample. This determination is made by checking if a response current measured via the detection electrodes 28, 29 exceeds the threshold value $I_1$ (See FIG. 5B). If the response current measured via the detection electrodes 28, 29 exceeds the threshold value $I_1$ (See FIG. 5B), it is assumable that the blood has reached at least a region around the detection electrodes 28, 29, so the capillary 25 has been filled with the blood. Thus, measurement of the response current using the detection electrodes 28, 29 enables to determine if the capillary 25 has been supplied with the target amount of blood.

In Step S9, the measurement of a response current for the determination may be made only once in a predetermined period of time after the beginning of the voltage application in Step S6, or may be repeated for a predetermined period of time.

If the detector 14 determines that the capillary 25 has not been filled with the target amount of blood (S9: NO), the detector 14 recognizes that this is an error due to insufficient blood supply (S10).

If the detector 14 determines that the capillary 25 has been filled with the target amount of blood (S9: YES), or the detector 14 recognizes that there has been an error in Step S10, the arithmetic operator 17 calculates glucose concentration based on a response current upon the lapse of the predetermined period of time (S11). The calculation of the glucose concentration is made on the basis of e.g. a predetermined calibration curve or lookup table which relates the response current to the glucose concentration.

A result of the calculation (blood sugar level) given by the arithmetic operator 17 is displayed on the display 18 (S12). On the other hand, if the detector 14 recognizes an error (S8, S10) (S13: YES), an error message is displayed on the display 18 (S14). The error message may simply be that the measurement was not successful, or may include more detailed information (e.g. blood movement or insufficient supply of blood).

The sample analyzer 1 ceases the concentration measuring operation if Step S1 finds that no biosensor 2 is attached (S1: NO), if the detector 14 recognizes no error (S8, S10) in Step S13 (S13: NO), or if an error message is displayed (S14).

It should be noted here that the determination if the blood has been moved (S7) and the determination if the target amount of blood has been supplied (S9) may be made after the calculation of the glucose concentration (S11). Further, Steps S7 and S9 may be swapped with each other.

According to the present embodiment, a voltage application for obtaining a response current which is necessary for calculating blood glucose level is made first, and thereafter, a voltage application for obtaining a response current which is necessary for detecting if a target amount of blood has been supplied. In other words, no voltage application is made for obtaining a response current necessary for the detection, during the time when a response current for the calculation is being obtained. Therefore, during the voltage application for detecting blood supply, no consumption is made on the reductant of electron transfer material which reflects the glucose concentration and thus must be retained until a response current for calculation has been obtained. Likewise, no disturbance is made to a uniform concentration of the reductant of electron transfer material when obtaining a response current for calculation. As a result, measuring accuracy is not decreased by the detection of blood supply.

According to the present embodiment, further, even when the detector 14 recognizes an error (S8, S10), blood sugar level is calculated (S11) and the calculation result is displayed (S12). Therefore, as compared with a case in which the measuring operation is simply ceased upon an error, the user can anyway obtain a result of measurement even if there has been an error during the measuring operation and the measurement result can only be useful as a reference data. As a result, it becomes possible to reduce meaningless use of the biosensors. Further, displaying an error message (S14) enables to make clear that the measuring result on the display 18 is a reference data, and further, displaying a detailed error message enables for the user to learn from the failure and not repeat the same mistake.

Obviously, the present invention is not limited to the form of embodiment thus far described. For example, the electrodes formed in the biosensor 2 maybe three, i.e. one detection electrode, one working electrode and one counter electrode. In this case, detection of sample supply will be made by using the detection electrode and the working electrode (or the counter electrode).

A voltage application in order to obtain a response current for detecting sample introduction and a voltage application to obtain a response current for calculation may not necessarily be made continuously. In other words, the voltage application may be stopped upon detection of sample introduction, and then resumed in a predetermined period of time in order to obtain a response current for calculation.

The present embodiment uses an amperometric technique in the measurement of blood glucose level, and the description was made accordingly. However, the present invention is also applicable to measurement of blood glucose level using a coulometric technique. When using a coulometric technique, measurement of response current is made for e.g. a predetermined period of time upon detection of blood introduction after a voltage application, and the blood glucose level is calculated from the electric quantity obtained by accumulating these response currents. After the obtainment of the response current values for calculation, additional application of voltage is made in order to obtain a response current for detecting if the sample has been introduced appropriately. On the other hand, whether the blood has moved or not is determined by checking the time course of electric quantity, to see if an inflexion point appears or not. Specifically, as shown in a long-dashed-double-short-dashed line in FIG. 5B, the electric quantity increases straightly with time if there is no blood movement. On the other hand, as shown in a long-dashed-double-short-dashed line in FIG. 5C, an inflexion point Q appears in the time graph of electric quantity if there is a blood movement. Therefore, it is possible to detect a blood movement by checking if there appears an inflexion point Q.

The invention claimed is:

1. A sample analyzing method based on a response obtained upon application of a voltage to a reaction field containing a sample, comprising:
   a preliminary step for introducing the sample;
   a first step performed later than the preliminary step for measuring a first response for use in calculation necessary for analyzing the sample; and
   a second step performed later than the first step for measuring a second response necessary to determine whether a target amount of the sample has been supplied to the reaction field;
   wherein the application of voltage to the reaction field in the first and the second steps is made by using two electrodes selected from three or more electrodes, and a combination of the two electrodes selected in the first step differs from a combination of the two electrodes selected in the second step.

2. The sample analyzing method according to claim 1, wherein the first and the second responses are measured as electric currents in the first and the second steps.

3. The sample analyzing method according to claim 1, wherein use is made of an analyzing tool which includes a substrate provided with a capillary for moving the sample, the substrate being also provided with said three or more electrodes, each of the electrodes having a respective part lined up in the capillary in a direction of the sample movement.

4. The sample analyzing method according to claim 3, wherein at least one of the two electrodes selected for measurement of the second response in the second step has its part disposed downstream of the sample flow from the two electrodes selected in the first step.

5. The sample analyzing method according to claim 1, further comprising a third step for determining whether or not the sample has moved in the reaction field while carrying out the first step.

6. The sample analyzing method according to claim 5, wherein the first response is measured at a plurality of measuring points at every predetermined time interval in the first step,
   the determination in the third step on whether or not the sample has moved in the reaction field being made by checking a time course of the responses obtained from the measuring points to see whether or not a first peak which appears first is followed by a second peak.

7. The sample analyzing method according to claim 6, wherein the first response is measured as a response current at each of the measuring points in the first step,
   the determination in the third step on whether or not the second peak has appeared being made by comparing a response current measured at one of the measuring points with a response current measured at another of the measuring points located right before said one measuring point in the time course, and by checking if the response current at said one measuring point exceeds the response current at said another measuring point by a predetermined or greater value.

8. The sample analyzing method according to claim 5, wherein the first response is measured at a plurality of measuring points at every predetermined time interval in the first step,
   the determination in the third step on whether or not the sample has moved in the reaction field being made by checking a time course of accumulated response values obtained from each measuring point to see whether or not there has appeared an inflexion point.

9. A sample analyzing method based on a response obtained upon application of a voltage to a reaction field containing the sample, comprising:
   a step of measuring a response at a plurality of measuring points at every specific time interval for use in calculation necessary for analyzing the sample; and an additional step of determining whether or not the sample has moved in the reaction field;
   wherein the determination in the additional step on whether or not the sample has moved in the reaction field being made by checking a time course of the responses obtained from the measuring points to see whether or not a first peak which appears first is followed by a second peak.

10. The sample analyzing method according to claim 9, wherein the response is measured as a response current at each of the measuring points,
   the determination in the additional step on whether or not the second peak has appeared being made by comparing a response current measured at one of the measuring points with a response current measured at another of the measuring points located right before said one measuring point in the time course, and by checking if the response current at said one measuring point exceeds the response current at said another measuring point by a predetermined or greater value.

11. A sample analyzing method of analyzing a sample based on a response obtained upon application of a voltage to a reaction field containing the sample, comprising:

a step of measuring a response at a plurality of measuring points at every specific time interval for use in calculation necessary for analyzing the sample; and an additional step of determining whether or not the sample has moved in the reaction field;

wherein the determination in the additional step on whether or not the sample has moved in the reaction field is made by checking a time course of accumulated response values obtained from each measuring point to see whether or not there has appeared an inflexion point.

12. A sample analyzer comprising:

a voltage applier for application of a voltage to a reaction field including a sample;

a response measurer for measurement of a response to the voltage applied to the reaction field;

a selector for selecting a first voltage application state for measurement of a first response for use in calculation necessary for analyzing the sample after the sample is introduced to the reaction field, or a second voltage application state for measurement of a second response for use in determining whether or not the reaction field has been supplied with a target amount of the sample;

an arithmetic operator for calculation necessary for analyzing the sample based on the first response;

a determiner for determination based on the second response, on whether or not the reaction field has been supplied with the target amount of the sample;

a controller for causing the selector to select the second voltage application state after causing the selector to select the first voltage application state; and an additional determiner for determining whether or not the sample has moved in the reaction field while measuring the first response;

wherein the sample analyzer is configured to utilize an analyzing tool including a substrate, a capillary for moving of the sample and three or more electrodes formed in the substrate, part of each electrode being lined up in the capillary in a direction of the moving of the sample, the voltage applier applying the voltage to the reaction field via two electrodes selected from the three or more electrodes, the controller controlling the selector in selecting the two electrodes for measurement of the second response to include at least one electrode a part of which is disposed downstream of the direction of the moving of the sample relative to the two electrodes selected for measurement of the first response, the arithmetic operator recognizing an error upon determination by the determiner of not receiving a supply of a target amount of the sample or upon determination by the additional determiner of a movement of the sample, the arithmetic operator making calculation necessary for analyzing the sample regardless of the error.

13. The sample analyzer according to claim 12, wherein the measurer measures the first and the second responses as electric currents in the first and the second steps.

14. The sample analyzer according to claim 12, wherein the selector includes a switch for individual selection for the three or more electrodes, of a state in which the electrode is electrically connected with the voltage applier or a state in which it is not.

15. The sample analyzer according to claim 12, further comprising a display for displaying a result of calculation made by the arithmetic operator and an error message.

16. The sample analyzer according to claim 15, wherein the display displays a content of the error upon recognition of the error by the arithmetic operator.

* * * * *